（12) United States Patent
Jämsen

(10) Patent No.: US 7,198,607 B2
(45) Date of Patent: Apr. 3, 2007

(54) DETECTOR UNIT, AN ARRANGEMENT AND A METHOD FOR MEASURING AND EVALUATING FORCES EXERTED ON A HUMAN BODY

(75) Inventor: Ari Jämsen, Oulu (FI)

(73) Assignee: Newtest Oy, Oulu (FI)

( * ) Notice: Subject to any disclaimer, the term of this patent is extended or adjusted under 35 U.S.C. 154(b) by 253 days.

(21) Appl. No.: 10/499,564

(22) PCT Filed: Dec. 18, 2002

(86) PCT No.: PCT/FI02/01038

§ 371 (c)(1),
(2), (4) Date: Jun. 21, 2004

(87) PCT Pub. No.: WO03/055389

PCT Pub. Date: Jul. 10, 2003

(65) Prior Publication Data

US 2005/0075586 A1    Apr. 7, 2005

(30) Foreign Application Priority Data

Dec. 21, 2001    (FI) .................................. 20012547

(51) Int. Cl.
A61B 5/103    (2006.01)
A61B 5/117    (2006.01)
A61B 5/00    (2006.01)

(52) U.S. Cl. ...................... 600/595; 600/587; 600/300

(58) Field of Classification Search ................ 600/587, 600/595

See application file for complete search history.

(56) References Cited

U.S. PATENT DOCUMENTS

| 4,524,243 | A | | 6/1985 | Shapiro |
| 5,125,412 | A | * | 6/1992 | Thornton ..................... 600/483 |
| 5,749,372 | A | | 5/1998 | Allen et al. |
| 6,059,576 | A | * | 5/2000 | Brann ......................... 434/247 |
| 6,183,425 | B1 | * | 2/2001 | Whalen et al. ............. 600/592 |
| 6,454,705 | B1 | * | 9/2002 | Cosentino et al. .......... 600/300 |
| 2001/0044362 | A1 | | 11/2001 | Morrow |

FOREIGN PATENT DOCUMENTS

WO    99/07280    2/1999

* cited by examiner

*Primary Examiner*—Max F. Hindenburg
*Assistant Examiner*—Anuradha Roy
(74) *Attorney, Agent, or Firm*—Volpe & Koenig, P.C.

(57) ABSTRACT

The invention relates an arrangement (10) for measuring and presenting forces exerted on body, describing the amount and intensity of physical exercise. The arrangement according to the invention comprises a detector unit (11), a communications device (13), a server (14) and a database (16) connected therewith, and a data presentation means (18). Furthermore, the invention relates to a detector unit (11) used in the arrangement and a method using the arrangement for measuring and analyzing the effectiveness and amount of physical exercise.

33 Claims, 2 Drawing Sheets

Figure 1:
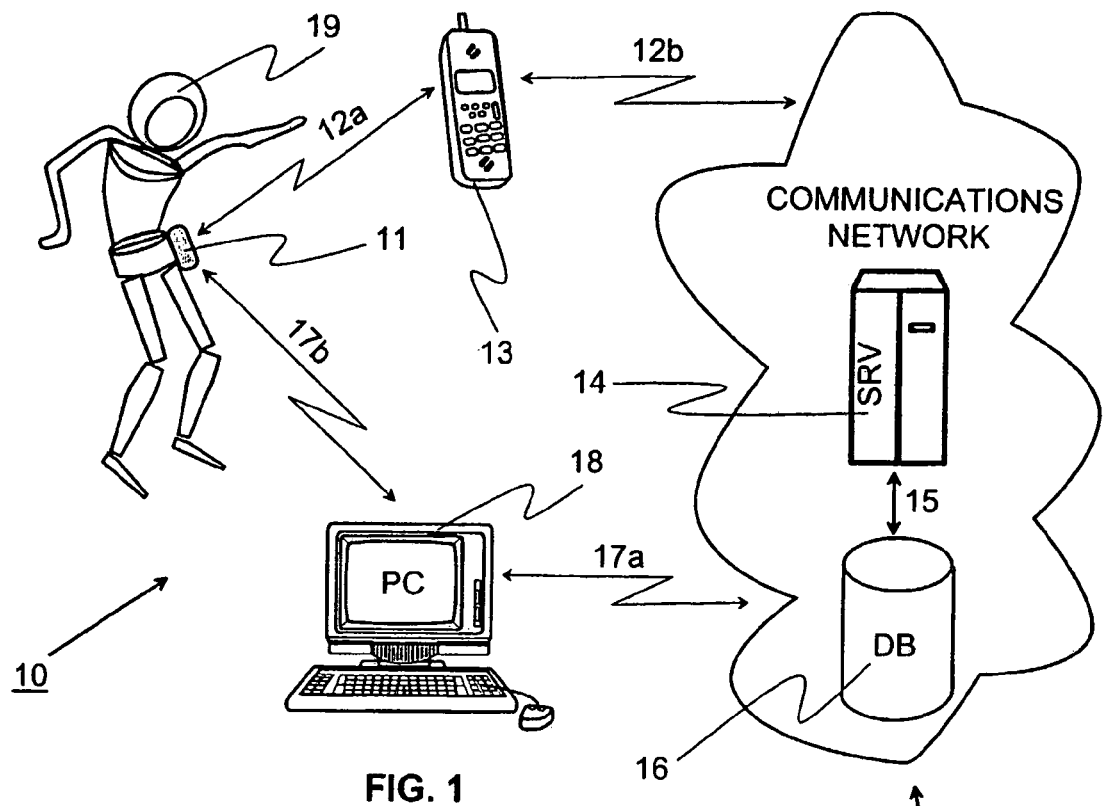

DETECTOR UNIT, AN ARRANGEMENT AND A METHOD FOR MEASURING AND EVALUATING FORCES EXERTED ON A HUMAN BODY

The invention relates to a detector unit for measuring, analysing and presenting acceleration data describing forces exerted on a person's skeletal system in conjunction with the person's activity performance, which detector unit comprises at least one acceleration sensor and a processing unit with a memory for making a first session-specific analysis based on the acceleration data and for storing the results of that analysis.

The invention also relates to an arrangement for measuring, analysing and presenting forces exerted on a person's skeletal system in conjunction with the person's activity performance, which arrangement comprises a detector unit, communications device, server, database connected with the server, which database contains the person's activity performance history as well as various causal relations concerning different groups of people, and an apparatus applicable for presenting analysis results for presenting the analysis results.

The invention further relates to a method employing the detector unit and the arrangement.

It is generally known that the quantity and quality of physical activity performed by a person have a major effect on his or her present and future health. A known way of reducing the probability of a heart disease is to strain the heart through suitable exercise at a suitable exertion level. There are numerous methods and arrangements to monitor the quantity and quality of activity beneficial to the heart. One such known method is to measure the heartbeat rate during exercise/exertion by means of a special device the readings of which can be observed either in real time or in non-real time using data collected on a data collecting device. For users of heartbeat rate monitoring devices there are research data available on optimal heartbeat rate levels and durations of exercise sessions.

One such method, applicable also with a heartbeat monitor, is introduced in publication WO 149169. It discloses an arrangement suitable for personal use for measuring several different quantities such as the heartbeat rate, for example, describing the level of activity of a person. Results from the measurements are transmitted via a network to a server where the data are analysed as instructed by the user. The user can examine the results from the analysis by means of a device connected to the network.

Weight control is also one of the major factors contributing to a person's health on a general level. If a person's energy intake from food is greater than his or her daily consumption of energy, the surplus energy is stored in tissue, which inevitably leads to weight increase. There is an obvious need for an easy-to-use calorimeter which would measure a person's energy consumption continuously and effortlessly.

One solution is presented in patent document U.S. Pat. No. 5,749,372. It discloses a portable apparatus which uses acceleration measurements to monitor the intensity of physical activity performed by a person. The apparatus gives to the user different audible tones when a given predetermined activity level is reached. The goal may be e.g. to consume a certain amount of energy per day. If desired, measurement results from several days can be stored on the apparatus, and the results can be transferred to an external device via a separate interface unit. An acceleration sensor in the apparatus is used to measure the activity level.

Like heart diseases, accelerated bone loss or osteoporosis is a widespread disease all around the world. Osteoporosis is a disease mainly suffered by the older generation, or at least it manifests in older people. However, if osteoporosis is to be prevented by leading a healthy life, attention has to be paid to bone loss prevention already in the childhood. Moreover, there is a hereditary predisposition to osteoporosis in some people. A sufficient amount of right exercise as well as sufficient intake of calcium and vitamin D help maximise the growth of bone mass. However, the bone mass starts to shrink at about the age of 30. After that, the loss of bone mass progresses inevitably if nothing is done to prevent it. Women lose more bone mass than men. Especially after the menopause, the loss of bone mass may develop into a disease, osteoporosis. In osteoporosis, bone tissue loses a considerable amount of mineral, calcium, as well as connective tissue. A bone may lose up to 20% of its mass in 5 to 7 years. A bone made brittle by advanced osteoporosis may break as a result of even a small strain. The hip bone, femur and wrist bones are especially prone to break, and in a person suffering from osteoporosis these may break as a result of a fall which need not even be serious.

Bones can be made stronger and osteoporosis prevented by living healthily, following a well-balanced diet and performing weight-bearing exercises to a sufficient extent. Suitable weight-bearing exercise can increase bone mass by about 3 to 5%. Already this bone mass increase helps prevent 20 to 30% of fractures caused by osteoporosis. Research shows that exercise in which sufficient forces, such as accelerations and decelerations, are exerted on the skeletal system or in which sufficient torsional strain is exerted on a limb/bone are beneficial to bone mass growth (The Lancet, vol. 348, Nov. 16, 1996, pp. 1343–1347). Such exercise includes different jumps, stepping, walking, running, climbing the stairs and bodily work. To prevent bone mass loss a person should know what kind of exercise and how much he or she should perform and, in addition, he or she should keep it up for years on end.

Exercise reduces the risk of fractures in other ways, too, in a person suffering from osteoporosis. Physical activity makes the muscles stronger and helps maintain motoric ability. This reduces the probability of falling and, hence, the risk of injury in general.

While it has been proven that exercise helps prevent bone diseases, prior-art methods and arrangements do not provide simple tools for long-term, effective and conscious utilisation of exercise in this respect. For example, data produced by commercially sold heartbeat monitors of today will tell whether a person is performing heart-straining activity or not. But the heartbeat monitoring data cannot be used to determine how the activity performed has improved the condition of the bones of the person. So, it is a matter of guessing whether the activity performed produced the desired result and whether the activity contributed to bone mass growth or helped maintain the existing bone mass.

Patent application document WO 99/07280 discloses a method and an arrangement for assessing a person's current bone quality. In this method, a person is exposed to vibration at a certain frequency for the duration of a measurement. This makes the person's combined muscular and bone tissue vibrate. According to the patent document, the vibration of the combined muscular and bone tissue can be utilised to determine the person's bone quality, i.e. also whether the person is suffering from osteoporosis or not. However, the bone density measurement according to this patent application document is always a one-time event and can be used only to assess the current condition of the bone measured, and no conclusions can be made about the future condition of the bones solely on the basis of the measurement made.

In order to improve his or her health a person should go on exercising through the rest of his or her life and he or she should at all times know what kind of exercise and how much is good for him or her. To achieve this goal a person needs a means to carry out activity-related measurements and to maintain an activity-related history. In this case, too, an easy-to-use equipment is needed so that data accumulated by the equipment can be utilised for determining the amount, intensity and type of exercise performed by the person using the equipment. These data can also be used to make deductions about the effectiveness of the exercise as regards its effect on the bone mass and the future development thereof.

An object of the present invention is to provide a new kind of activity measurement method and arrangement with which it is easy to monitor the quantity and quality of exercise performed by a person, especially as regards forces exerted on the skeletal system.

The objects of the invention are achieved by an arrangement in which measurement data describing the magnitude and quantity of forces exerted on the skeletal system of a person are continuously collected during daily exercise, and information about an analysis, which is from time to time made on the data collected, is sent to the person performing the exercise in order to indicate the amount, intensity and type of exercise performed.

A detector unit according to the invention for measuring and presenting forces exerted on the skeletal system during an exercise performance is characterised in that a processing unit in the detector unit is arranged so as to utilise data from an acceleration sensor, which data comprise peak values of measured momentary acceleration values and the number of said acceleration peak values during a session, and a first analysis means for making an assessment on the development of bone mass in a first analysis.

An arrangement according to the invention is characterised in that it comprises a server arranged so as to use a second analysis means and database information at the server about peak values for measured momentary acceleration values and the number of said acceleration peak values during a session in a second analysis for making an assessment on the development of bone mass.

A measuring and presenting method for forces exerted on the skeletal system of a body during an exercise performance is characterised in that an analysis means used in the method is utilised to make an assessment on the development of bone mass based on measurement data from an acceleration sensor, which measurement data comprise peak values of measured momentary acceleration values and the number of said acceleration peak values during a session.

Some advantageous embodiments of the invention are specified in the dependent claims.

The basic idea of the invention is as follows: A person carries along a lightweight detector unit which measures and records acceleration forces exerted on the skeletal system of his or her body during daily or other exercise. Acceleration means in this context either an increase or decrease in kinetic velocity, the latter of which is often called deceleration. Results from the acceleration measurements are processed in the detector unit using a first analysis means. The detector unit may also include different computing algorithms for the first analysis means, such as a bone quality application or fitness activity application. If necessary, the detector unit can present the results of the first analysis on a coarse level. The acceleration measurement data are always temporarily saved to an electronic component in the detector unit. In a preferred embodiment of the invention, measurement data are sent forward from this electronic component through wireless technology to a second device by means of which it is possible to establish a communications connection with a network server used in a second analysis of the measurement results. The measurement data on the person's activity are thus transmitted to this server which makes a second, more detailed analysis of them using a second analysis means, and returns the result from the second analysis to a device which can indicate to the person how effective the exercise was as regards the strain on the skeletal system. The first and second analysis means are hereinafter called the analysis means. The method and arrangement according to the invention are intended to guide a person to perform a right kind of exercise helping him or her to achieve his or her personal goal.

An advantage of the invention is that the measurement data about the forces exerted on the skeletal system of a person during exercise can be kept up-to-date all the time without the person having to take any special measures.

Another advantage of the invention is that a person has access to up-to-date information on the basis of which he or she can monitor and adjust the amount and exertion level of his or her exercise according to his or her goal both on a daily level (first analysis) and over some selected interval (second analysis).

Another advantage of the invention is that a person will all the time have access to the different type-specific amounts of exercise which can be utilised, if necessary, to draw up a personal recommendation for additional exercise.

Another advantage of the invention is that non-performance by the exercising person will not affect the quantity and quality of the measurement data collected.

Another advantage of the invention is that same measurements can be utilised e.g. in calculating the energy consumption of the person.

The invention will be now described in detail. The description refers to the accompanying drawings in which FIG. 1 shows, as an example, component parts of an arrangement according to a preferred embodiment of the invention, FIG. 2 shows, as an example, a portable personal detector unit belonging to an arrangement according to the invention, and FIG. 3 shows, as an example, a flow diagram of the method for measuring, analysing and presenting forces exerted on the skeletal system which method utilises an arrangement according to the invention.

Figure 2:
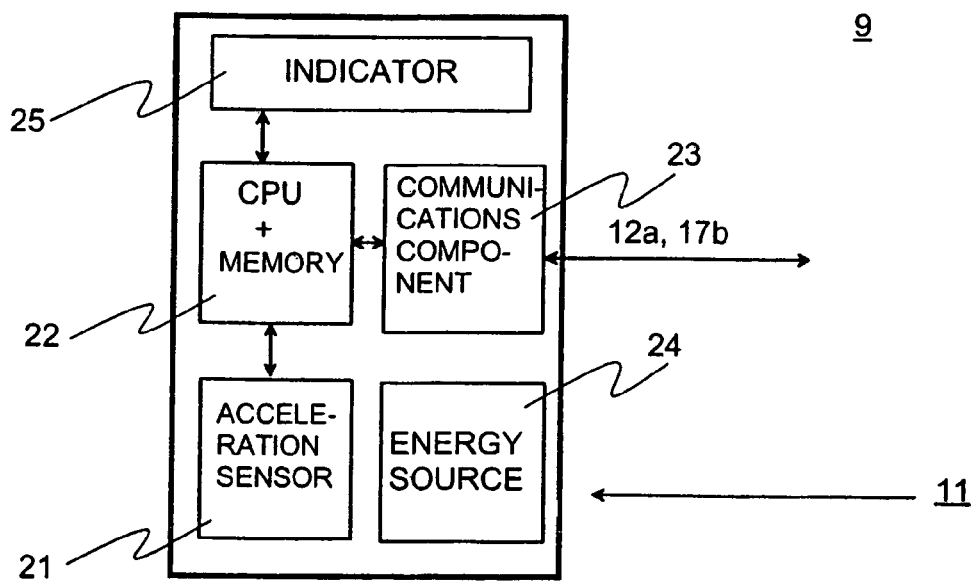
Figure 3:
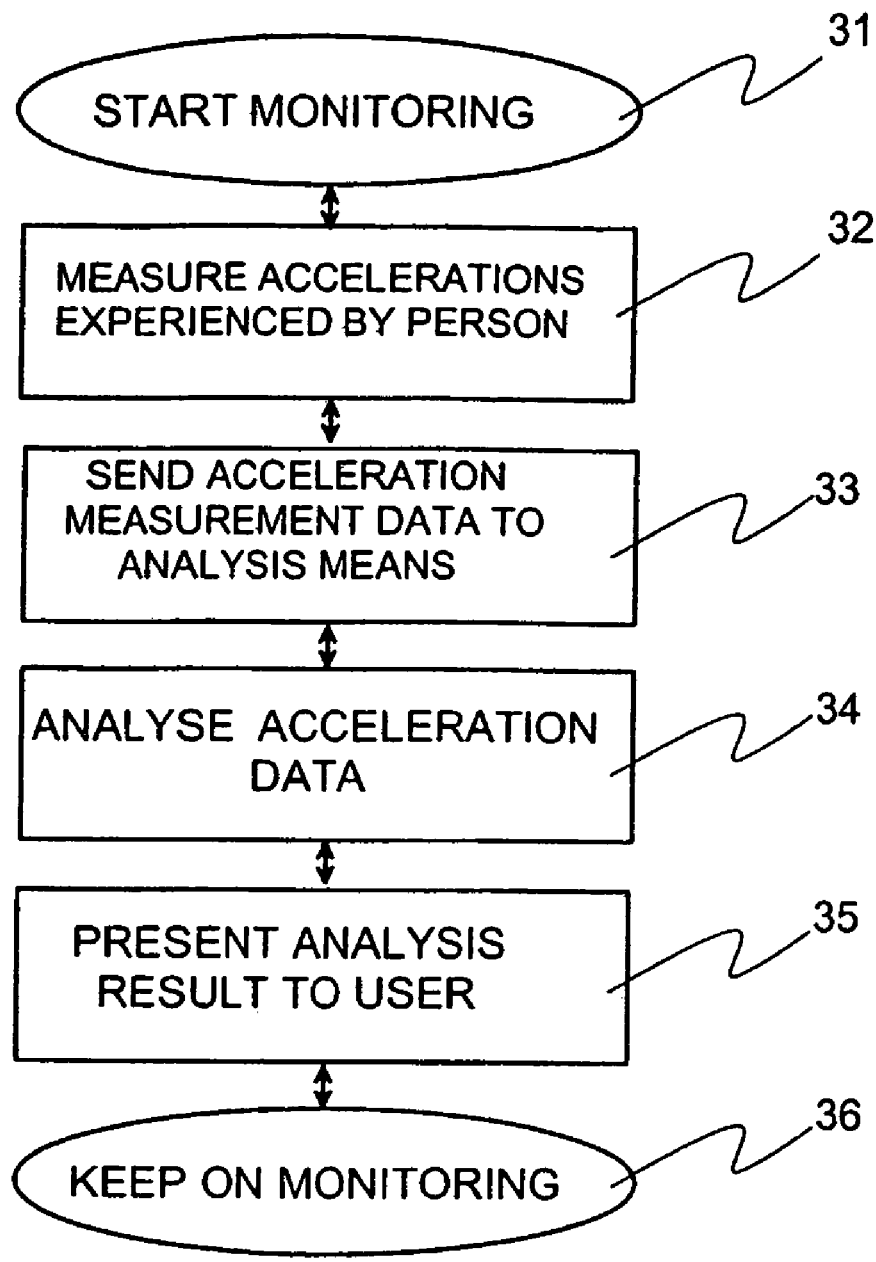

The examples depicted in FIGS. 1 to 3 illustrate some potential ways of utilising the arrangement and method according to the invention. FIG. 1 shows a preferred embodiment of the arrangement 10 which can be used to utilise the invention. The arrangement 10 is used to monitor the forces exerted on the skeletal system of a person 19 during his or her daily activities. Therefore, the person 19 carries on him or her a personal detector unit 11 which is advantageously attached to a belt or some other piece of clothing or accessory continuously on the person.

In the advantageous embodiment according to FIG. 1, the detector unit 11 measures forces exerted on the skeletal system of a person by continuously measuring accelerations exerted on his or her lower limbs. The detector unit 11 processes/analyses the measurement data by a first analysis means using an analysis algorithm appropriate for the user 19 of the device, and temporarily saves the results of the first analysis to a memory in the detector unit 11. In a preferred embodiment these data can be presented as session-specific information by a means of presentation connected with the detector unit 11. Saved results of the first analysis are transferred from the detector unit 11 advantageously through a wireless link 12a to a communications device 13. In the exemplary embodiment of FIG. 1, said communications device 13 is advantageously a mobile terminal adapted so as to function in a cellular network. Transfer 12a of the first analysis data from the detector unit 11 to the communications device 13 can advantageously take place via an infrared link or using a suitable radio link such as a TDMA (Time Division Multiple Access) link, CDMA (Code Division Multiple Access) link, Bluetooth link, or a WLAN (Wireless Local Area Network) link.

These analysis data can be further transmitted from the communications device 13 advantageously over one of the above-mentioned wireless communications links 12b to a public communications network 9 to be forwarded by that network to a server (SRV) 14 according to the invention, specialised in a more detailed second analysis of the information obtained through the arrangement according to the invention. In the analysis, the server 14 utilises the second analysis means according to the invention. The used communications network 9 is advantageously a conventional telephone network, cellular network or a network serving Internet connections. As far as the inventional idea is concerned, the exact nature of the communications network is irrelevant. The server 14 further includes a connection 15 with a database (DB) 16 which contains information about certain groups of people, needed in the more detailed second analysis of the measurement data.

Advantageously this database 16 contains data organised in appropriate categories such as sex, age, height, weight, hereditary disposition to some disease, as well as information, based on research, about an advantageous amount and level of exertion of forces exerted on the skeletal system per unit time according to the aforementioned criteria. Other information/causal relations advantageously included in the database 16 are energy consumption tables, known as such through research, and the relationship between the amount and exertion level of forces exerted during exercise on the skeletal system and the change in bone tissue mass. Advantageously the database 16 further includes analysis algorithms for various applications, which algorithms can be transferred via the communications network 9 to the detector unit 11, for example. One such analysis algorithm is an algorithm for monitoring the development of bone mass. As a basis for an analysis algorithm it is possible to utilise studies on bone mass development, published e.g. in: Lancet, 1196, Vol. 348, pp. 1343–1347; Journal of Bone and Mineral Research, 199, Vol. 14, pp. 125–128; and Medicine & Science in Sports & Exercise, 2000, Vol. 32, pp. 1051–1057.

An energy consumption algorithm, for instance, advantageously takes into account the person's weight, the absolute values and frequency of measured accelerations, and the time interval over which acceleration impulses were received. These data indicate whether the person is immobile, walking, jogging, or running at high speed. Based on these data it is possible to calculate the person's energy consumption during an exercise performance.

A bone mass development algorithm advantageously takes into account the basic personal data, the absolute values and the quantity of measured accelerations and advantageously also the type of exercise over a measurement interval. The measurement interval is advantageously of the order of one day, and said algorithm is used at the end of the measurement interval at the latest to compute an evaluation for the person about whether he or she has reached his or her exercise goal regarding bone mass development. This evaluation can be presented to the person either graphically in curves or the like or as a simple YES/NO message.

The server 14 receives via link 12b or 17a advantageously information concerning the identification of a person, such as sex, age, hereditary disposition etc. A unique ID code could also be transferred, in which case the other data relating to the person 19 are advantageously already stored in the database 16. In addition, the analysis/measurement data obtained from the detector unit 11 are always transferred. Based on the data available to it, the server 14 now carries out a more detailed second analysis which will show the effects of the amount and level of exercise performed. The result from the second analysis advantageously includes information relevant to the goals set by the person in question. Analysis data representing forces exerted on the skeletal system, for instance, could be presented as part of an analysis of health-related exercise. Based on the analysis, a personal recommendation for additional exercise could advantageously be made in order to reach the personal exercise performance goal. The result from the second analysis carried out at the server is saved in the database 16 as part of the history continuum of the person 19 in question.

The results from the second analysis carried out at the server 14 can be transferred from the database 16 via a link 17a to a device 18 suitable for presenting the analysis data. In the exemplary embodiment depicted in FIG. 1 this device 18 is advantageously a personal computer (PC). This device 18 displays to the person 19 the result from the second analysis carried out at the server 14. Based on this second analysis the person 19 can make conclusions about whether the amount or exertion level of the exercise should be changed in some way or another in order to reach the goals set. In an advantageous case, the results from the second analysis can be utilised to determine whether the amount and exertion level of the exercise was sufficient to increase the person's 19 bone mass.

Measured acceleration data, amplitude and direction of acceleration, which are stored at the server 14, can also be advantageously utilised for analysing and also presenting the type of exercise performed by the person during the measurement interval. Examples of such types of exercise include running, walking, stepping, or jumping sideways or up and down. Based on this analysis it is possible to recommend a certain type of additional exercise in order to reach the personal goal.

In an advantageous embodiment the arrangement 10 comprises a wireless communications link 17b between the detector unit 11 and the device 18 for presenting the information. In this embodiment, the first analysis data produced by the detector unit 11 can advantageously be transferred also via the device 18 to the server 14. The same communications link 17b can advantageously be utilised in the transfer of various messages to the detector unit 11. These messages may include instructions concerning the control of the detector unit 11, short indicator signals to the user 19 of the detector unit 11, or an instruction to send the analysis data recorded by the detector unit 11 to the device 18.

Through this communications link 17b it is also possible to install in the detector unit 11 a user-specific application ordered/purchased by the user, e.g. an application for analysing energy consumption for fitness-oriented exercise, or an application for analysing bone-mass-increasing exercise for a person interested in reducing the risk of osteoporosis. Naturally, there are numerous other applications involving the analysis of forces exerted on the skeletal system in addition to the applications mentioned above.

In an advantageous embodiment the cellular terminal 13 is used instead of a separate device 18 for presenting analysis data. This can be done already with existing cellular terminals, but future third-generation network terminals in particular will be capable of presenting the analysis data instead of the device 18.

In another advantageous embodiment the measuring sensors needed to measure the forces exerted on the skeletal system are connected with the person's cellular terminal 13. In that case the terminal 13 advantageously comprises a separate software application to collect, analyses save and, if necessary, send to a server 14 exercise measurement data. In an advantageous embodiment, commercially available analysis algorithms for analysing measurement data have been loaded to the terminal 13 e.g. from a database 16. In that case, the analysis and presentation of exercise data can be performed at the terminal 13.

In an advantageous embodiment, some of the analysis algorithms in the database 16 have been transferred to the detector unit 11 according to the invention. Advantageously this involves the information describing the exercise-related goals of the person in question. In that case, most of the daily or session-specific processing of measurement data can be performed already at the detector unit 11 using the first analysis means, and the result from the coarse analysis performed there can be advantageously presented as a session-specific analysis result on an indicator device connected with the detector unit 11.

Naturally, the session-specific results from the first analysis can be sent forward either to device 18 or to the server 14 for more detailed processing and presentation of the results/data. In this embodiment, advantageously only that part of the information processed which is needed for the person's 19 exercise history, is transferred to the database 16.

FIG. 2 shows an advantageous embodiment of the detector unit 11. The detector unit 11 advantageously comprises an energy source 24 such as a battery. The electric elements in the detector unit 11 get their energy from this energy source 24. There is at least one acceleration sensor 21 in the detector unit 11. Using more sensors 21 it is possible to measure accelerations in two or three dimensions, if required. The measuring range of an individual acceleration sensor is advantageously ±12 g.

Acceleration measurements made at the detector unit 11 can be utilised in various ways. In evaluating the energy consumption in fitness-oriented activity the acceleration data are analysed/integrated over the time used in the exercise. In evaluating bone mass development, it is used the number of sessions in excess of a certain acceleration value per suitable time unit, advantageously one day. Likewise, the acceleration measurement data produced by the detector unit 11 can be used to determine the type of exercise performed by the person and, accordingly, he or she can be given an appropriate recommendation for additional exercise if necessary.

In each application, the measurement data from the acceleration sensor 21 are sent to a central processing unit (CPU) 22 in the detector unit 11, which CPU 22 advantageously includes also a certain amount of memory available to it for storing different software applications and measurement results according to the invention. The CPU 22 advantageously makes a coarse analysis of measured acceleration data using a first analysis means, saved in its memory, according to a software application suitable for a certain type of exercise.

The first analysis means advantageously also comprises a means to determine, based on the measured amplitude and direction of acceleration, which type of exercise the person is performing. These measurement data can be utilised for obtaining the total amounts, total durations or relative portions of the various types of exercise performed by the person.

The CPU 22 is advantageously connected with a communications component 23. The communications component is used to establish communications links with either a cellular terminal, link 12a, or a device 18 suitable for presenting analysis data, link 17b. The communications component 23 advantageously supports at least one communications method. Advantageous methods for communication include infrared (IR) technology, Bluetooth technology, WLAN technology and different time or code division technologies used in cellular networks.

The detector unit 11 advantageously also includes an indicator means 25 e.g. for session-specific indication of the result from the first analysis. With the indicator means it is possible to signal, through simple ON/OFF type messages, to the user of the detector unit 11 whether the exercise performance over a given time interval is in accordance with the predetermined goal. The indicator means 25 may comprise one or more lamps/leds of different colours, buzzers, or analogue meters. In an advantageous embodiment, two leds of different colours are used to indicate whether the detector unit 11 is in measuring mode, whether activity has occurred at all during a given time period, and whether the activity has been in accordance with the predetermined goal. For example, a person performing fitness-oriented activity can be informed at the end of an exercise session about whether he or she has consumed a sufficient amount of energy with respect to his or her goal. Likewise, a person interested in developing his or her bone mass can be informed about whether a sufficient number of appropriate exertion impulses was received e.g. in the past 24 hours. More detailed analysis proper can be made later at a desired point of time at the server 14 on the basis of information stored in the database 16. The analysis made at the server 14 gives a more detailed picture concerning the achievement of the goal set by the person, because it also utilises the person's exercise history stored on the server earlier.

FIG. 3 shows, in the form of an exemplary flow diagram, main stages of the method according to the invention. The method can be used to produce an indication about whether the goal of the exercises performed by the person has been reached or not. Collection of measurement data is started at step 31. In that step the person 19 in question puts on a detector unit 11 according to the invention. In step 32 the detector unit uses acceleration measurements to continuously collect, when the person is moving, information about the forces exerted on his or her skeletal system, the absolute values of the forces, their frequencies and quantities. In different applications the measured acceleration data are processed using an appropriate analysis algorithm. The measurement data are temporarily saved to the memory of the detector unit 11. This way they can be indicated, if required, by the indicator means 25 in the detector unit 11 as session-specific results from the first analysis.

The session-specific measurement/analysis data stored by the detector unit 11, the first analysis, is sent either by the person 19 using the detector unit 11 or fully automatically to the second analysis means according to the invention, which advantageously comprises a software application running on a separate server 14, step 33. Fully automatic transfer can be realised using Bluetooth technology, for example. In that case the detector unit 11 sends the measurement data to a device connected with a communications network 9, either to a cellular terminal 13 or to a device 18 intended for presenting the analysis results, when it arrives in the service area of said devices. A service area means in this context an area within which a Bluetooth radio link can be established. This area is in practice of the order of a few dozen metres in an open space.

A more detailed second analysis of measurement data is advantageously made at the server 14 using the second analysis means. It utilises information stored in the database 16 concerning both personal data and general data about certain groups of people, step 34. The personal data include also all the analysis results for previously stored exercise data, which can be used to produce a more detailed evaluation about the achievement of long-term exercise goals. If the analysis plainly shows that the person should perform a certain type of additional exercise in order to reach his or her goal, a recommendation to that effect can be made to him or her.

In step 35 a communications link 17a is established between the server 14 and a device 18 suitable for presenting the information. Data, which have been more closely analysed at the server 14, can be displayed on the device 18. Based on this information it is possible to determine whether the physical exercise performed by the person was sufficient to reach the goal.

In some advantageous embodiments, part of the second analysis made at the server can be performed either at the terminal 13 or in the detector unit 11 if a suitable analysis algorithm has been loaded to them e.g. from the database 16. In that case the achievement of the daily or session-specific exercise goal can be determined without a more detailed long-term analysis at the server.

Collection of measurement data about the forces exerted on the skeletal system goes on all the time, step 36, also during the data processing steps described above.

Some advantageous embodiments of the invention were described above. The invention is not limited to the solutions just described. The objects of acceleration data measuring mentioned in the description are only examples of possible applications of the method according to the invention. The inventional idea can be applied in numerous ways within the scope defined by the attached claims.

The invention claimed is:

1. A detector unit for measuring, analysing and presenting acceleration data describing forces exerted on a person's skeletal system in conjunction with the person's activity performance, which detector unit comprises:
   at least one acceleration; and
   a processing unit with a memory for carrying out by a first analysis means a first session-specific analysis based on the acceleration data and for saving the results from that analysis, characterised in that the processing unit is arranged so as to utilise measurement data from an acceleration sensor, which data comprise peak values of measured momentary acceleration values and the number of said peak acceleration values during a session, and the first analysis means for making an assessment on the development of bone mass in the first causal analysis.

2. A detector unit according to claim 1, characterised in that at least one of the following is arranged to be produced on the basis of the peak values of measured momentary acceleration values and the direction of said accelerations: an evaluation of the type of exercise performed, an evaluation about a recommendation for additional exercise.

3. A detector unit according to claim 1, characterised in that it also comprises an indicator for indicating to the user of the detector unit the result from the first session-specific analysis.

4. A detector unit to claim 1, characterised in that it also comprises a communications component for enabling acceleration measurement data communication between the detector unit and an external communications device.

5. A detector unit according to claim 1, characterised in that an analysis algorithm, to be used in the processing of measured acceleration data, is arranged to be stored in the memory of the processing unit.

6. A detector unit according to claim 5, characterised in that the computing algorithm used in the first analysis is a computing algorithm for an exercise performance aimed to develop bone mass.

7. A detector unit according to claim 3, characterised in that the indicator is of ON/OFF type where ON indicates achievement of the session-specific goal of an exercise performance, and OFF indicates non-achievement of the goal of an exercise performance.

8. A detector unit according to claim 7, characterised in that the indicator is implemented using two leds of different colours so that ON state is indicated by turning on one led, and OFF state is indicated by turning on the other led.

9. A detector unit according to claim 1, characterised in that the acceleration sensor in the detector unit is arranged so as to measure accelerations in the range ±12 g.

10. A detector unit according to claim 4, characterised in that the communications component comprises a means for handling communication between a communications device and a device suitable for presenting the analysis results based on one of the following: infrared technology, time division multiple access (TDMA) technology, code division multiple access (CDMA) technology, Bluetooth technology, WLAN technology.

11. A detector unit according to claim 1, characterised in that the detector unit is fabricated as part of the electronic construction of a communications device.

12. A detector unit according to claim 11, characterised in that the communications device is a cellular terminal.

13. An arrangement for measuring, analysing and presenting forces exerted on the skeletal system of the body of a person during an exercise performance, which arrangement comprises:
   a detector unit comprising a means for measuring, by means of acceleration measurements, forces exerted on the skeletal system of a body during an exercise performance, and a first analysis means for carrying out a first session-specific analysis based on said measurement results, and a means for saving and presenting the results from the first analysis,
   a communications device to which the results from the first analysis are to be transferred over a wireless link,
   a server to which the results from the first analysis are to be transferred from the communications device via one or more communications networks for a second analysis of the acceleration measurement data,
   a database connected with the server, which database contains an exercise history of a person and different causal relations concerning various groups of people, and
   a device suitable for presenting the results from the second analysis, to which device the results from the second analysis, processed by the server, are to be transferred via a communications network, which second analysis describes the quantity and exertion level of the forces exerted on the skeletal system of a body during an exercise performance, characterised in that the server is arranged to utilise in the second analysis the second analysis means and data saved in the database about the peak values of measured momentary acceleration values and the number of said peak acceleration values during a session for producing an evaluation of bone mass development.

14. An arrangement according to claim 13, characterised in that at least one of the following is arranged to be produced on the basis of the peak values of measured momentary acceleration values and the direction of said accelerations: an evaluation of the type of exercise performed, an evaluation about a recommendation for additional exercise.

15. An arrangement according to claim 13, characterised in that the wireless communications link between the detector unit and communications device is one of the following: infrared link, Bluetooth link, WLAN link or a cellular telephone link.

16. An arrangement according to claim 13, characterised in that the communications device is a cellular terminal.

17. An arrangement according to claim 13, characterised in that the communications network is one of the following: conventional telephone network, cellular network, or an Internet-based network.

18. An arrangement according to claim 13, characterised in that the server comprises:
  a means for receiving the results from a first analysis describing the quantity and exertion level of forces exerted on the skeletal system of a body during an exercise performance,
  a means for obtaining from the database a person's exercise history,
  a means for obtaining from the database causal relation data concerning various groups of people,
  a second analysis means for performing on the basis of said information a second analysis describing the quantity and exertion level of forces exerted on the skeletal system of a body during an exercise performance,
  a means for converting the results of the analysis into a presentable form, and
  a means for transferring the presentable results of the second analysis via a communications network to a suitable device available to the user.

19. An arrangement according to claim 18, characterised in that the database part which describes causal relations concerning various groups of people contains data as follows: personal identification data, sex, age, height, weight, relation of measured absolute values and quantities of acceleration to bone mass development as well as a person's hereditary disposition to certain diseases.

20. An arrangement according to claim 18, characterised in that the second analysis means for performing on the basis of said data a second analysis describing the quantity and exertion level of forces exerted on the skeletal system of a body during an exercise performance comprises an algorithm for analysing an exercise performance aimed to develop or maintain bone mass.

21. An arrangement according to claim 13, characterised in that the device suitable for presenting the results of the analysis of an exercise performance is either a personal computer (PC) or a cellular terminal.

22. An arrangement according to claim 13, characterised in that the communications device and the device suitable for presenting the results of the analysis are one and the same device, and the device is either a personal computer (PC) or a cellular terminal.

23. An arrangement according to claim 13, characterised in that it also comprises a wireless communications link between the device suitable for presenting the results of the analysis and the detector unit for transferring control inforation to the detector unit.

24. An arrangement according to claim 23, characterised in that the control information transferred to the detector unit comprises a computing algorithm for an exercise performance aimed to develop or maintain bone mass.

25. A method for measuring, analysing and presenting, based on acceleration measurements, data describing forces exerted on the skeletal system of the body of a person during an exercise performance, which method comprises:
  a step in which the person performing a physical exercise has on him or her a detector unit measuring acceleration data in order to continuously measure the quantity and exertion level of accelerations experienced by the skeletal system of the body of the person,
  a step in which said acceleration measurement data continuously measured by the detector unit are transferred to a first or second analysis means,
  a step in which said measurement data are analysed by analysis means, and
  a step in which the results from the analysis are presented in order to evaluate the effects of the amount and exertion level of the forces exerted on the body of the persons characterised in that the analysis means is used for making an evaluation of the development of bone mass on the basis of the measurement data obtained from an acceleration sensor, which data comprise peak values of measured momentary acceleration values and the number of said peak acceleration values during a session.

26. A method according to claim 25, characterised in that at least one of the following is arranged to be produced on the basis of the peak values of measured momentary acceleration values and the directions of said accelerations: an evaluation of the type of exercise performed, an evaluation about a recommendation for additional exercise.

27. A method according to claim 25, characterised in that the step for processing the measurement data in an analysis means comprises a first analysis by the first analysis means in the detector unit.

28. A method according to claim 27, characterised in that the step for processing the measurement data for the analysis means also comprises:
  a step in which the acceleration measurement data measured by the detector unit or the first analysis data are transferred to a communications device through a wireless link, and
  a step in which the acceleration measurement data/first analysis data are transferred from the communications device to the second analysis means via a public communications network.

29. A method according to claim 25, characterised in that the step for analysing the measurement data by the second analysis means comprises:
  a step in which the measurement data concerning accelerations exerted on the body, measured by the detector unit, or the first analysis data, are saved to the memory of a server, a step in which causal relations concerning various groups of people corresponding to the identification information of a person are looked up in a database in the server, and a step in which the data obtained from the database are matched against the data received from the detector unit, the second analysis, and a step in which the result from the second analysis is saved to the memory of the server.

30. A method according to claim 25, characterised in that the step for presenting the results from the second analysis by a device suitable for presenting the analysis data comprises:

a step in which the results of the second analysis are transferred via a communications network from the server to the device suitable for presenting the analysis data, and a step in which said results of the second analysis computed for evaluating the amount and intensity of forces exerted on the body are presented by the device suitable for presenting the analysis data.

31. A method according to claim 30, characterised in that the device suitable for presenting the analysis results is one of the following: a personal computer, a cellular terminal.

32. A method according to claim 25, characterised in that the step for evaluating the amount and exertion level of the forces exerted on the body also comprises indication of a session-specific result of the first analysis made in the detector unit by means of an indicator belonging to the detector unit.

33. A method according to claim 25, characterised in that measured acceleration data are processed in the analysis means using a computing algorithm for exercise performance.

* * * * *